(12) United States Patent
Sugimoto (10) Patent No.: US 9,041,582 B2
(45) Date of Patent: May 26, 2015

(54) ORGANISM STATE QUANTITY MEASURING APPARATUS

(71) Applicant: OLYMPUS CORPORATION, Tokyo (JP)

(72) Inventor: Naoya Sugimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 173 days.

(21) Appl. No.: 13/736,359

(22) Filed: Jan. 8, 2013

(65) Prior Publication Data

US 2013/0201049 A1 Aug. 8, 2013

Related U.S. Application Data

(63) Continuation of application No. PCT/JP2011/055793, filed on Mar. 11, 2011.

(30) Foreign Application Priority Data

Jul. 16, 2010 (JP) ................................. 2010-161812

(51) Int. Cl.
*H03M 1/82* (2006.01)
*H03M 1/52* (2006.01)
(Continued)

(52) U.S. Cl.
CPC ............. *H03M 1/52* (2013.01); *A61B 5/14532* (2013.01); *A61B 5/1459* (2013.01); *G01N 21/6428* (2013.01)

(58) Field of Classification Search
CPC .... H03M 1/52; A61B 5/14532; A61B 5/1459
USPC .................. 341/167, 155, 118, 120
See application file for complete search history.

(56) References Cited

U.S. PATENT DOCUMENTS

| 4,633,491 A | * | 12/1986 | Kuhnel | ............................ | 377/20 |
| 4,909,633 A | * | 3/1990 | Okui et al. | ..................... | 356/405 |

(Continued)

FOREIGN PATENT DOCUMENTS

| CN | 1276709 A | 12/2000 |
| CN | 1335756 A | 2/2002 |

(Continued)

OTHER PUBLICATIONS

Abstract of International Publication No. WO 00/74753 A1, dated Dec. 14, 2000 (corresponding to JP 3683856).
International Search Report dated Jun. 14, 2011 issued in PCT/JP2011/055793.

*Primary Examiner* — Peguy Jean Pierre
(74) *Attorney, Agent, or Firm* — Scully, Scott, Murphy & Presser P.C.

(57) ABSTRACT

An apparatus including a detecting unit that detects information indicating a state of an organism from the organism or an organism specimen extracted from the organism and outputs the detected information as a current, a current-voltage conversion circuit that converts the current output from the detecting unit into a voltage, a double-integration-type A/D conversion circuit having an integration capacitor that is charged based on a voltage output from the current-voltage conversion circuit and is thereafter discharged, and a counter that measures a charge time during which the integration capacitor is charged and a discharge time during which the integration capacitor is discharged, the A/D conversion circuit converting into digital quantities the charge time and the discharge time measured by the counter, and outputting the digital quantities, and an information processing unit that calculates a state quantity of the organism based on the digital quantities output from the A/D conversion circuit.

6 Claims, 7 Drawing Sheets

(51) Int. Cl.
*A61B 5/145* (2006.01)
*A61B 5/1459* (2006.01)
*G01N 21/64* (2006.01)

(56) References Cited

U.S. PATENT DOCUMENTS

| | | | | |
|---|---|---|---|---|
| 4,942,877 | A | * | 7/1990 | Sakai et al. .................... 600/323 |
| 4,965,578 | A | * | 10/1990 | Poujois ......................... 341/156 |
| 5,614,902 | A | * | 3/1997 | Hopkins ........................ 341/118 |
| 6,016,115 | A | * | 1/2000 | Heubi ........................... 341/161 |
| 7,199,594 | B2 | * | 4/2007 | Kermani ........................ 324/663 |
| 7,990,305 | B2 | * | 8/2011 | Park et al. ..................... 341/167 |

FOREIGN PATENT DOCUMENTS

| | | |
|---|---|---|
| EP | 1 027 861 A1 | 8/2000 |
| JP | 3683856 | 6/2005 |
| JP | 2007-222669 | 9/2007 |
| JP | 2007-525858 A | 9/2007 |
| JP | 2009-271010 | 11/2009 |
| JP | 2011-120618 | 6/2011 |
| WO | 00/32099 A1 | 6/2000 |
| WO | 2004/093504 A2 | 10/2004 |
| WO | WO 2009/067626 A1 | 5/2009 |

* cited by examiner

ORGANISM STATE QUANTITY MEASURING APPARATUS

CROSS-REFERENCE TO RELATED APPLICATION

This is a continuation of International Application PCT/JP2011/055793, with an international filing date of Mar. 11, 2011, which is hereby incorporated by reference herein in its entirety.

BACKGROUND OF THE INVENTION

1. Field of the Invention

The present invention relates to an organism state quantity measuring apparatus.

2. Description of Related Art

Among apparatuses for injecting insulin into an organism, an apparatus is conventionally known that measures the glucose level in an organism and controls the amount of injection of insulin according to the measured value obtained (see, for example, the publication of Japanese Patent No. 3683856). An analog signal for the measured glucose level is converted into a digital signal by an A/D converter having an integration circuit, and the digital signal is processed.

However, Characteristic values such as an electrostatic capacitance and a resistance value of circuit elements such as a capacitor and a resistor constituting the integration circuit change with time depending on the time during which the circuit elements are used and the environment surrounding the circuit elements, for example. At that time, in the case of the apparatus according to Japanese Patent No. 3683856, the output from the integration circuit changes with changes in characteristic values of the circuit elements and it is difficult to obtain an accurate measured output value.

BRIEF SUMMARY OF THE INVENTION

According to one aspect of the present invention, there is provided an organism state quantity measuring apparatus including a detecting unit that detects information indicating a state of an organism from the organism or an organism specimen extracted from the organism and outputs the detected information as a current, a current-voltage conversion circuit that converts the current output from the detecting unit into a voltage, a double-integration-type A/D conversion circuit having an integration capacitor that is charged based on a voltage output from the current-voltage conversion circuit and is thereafter discharged, and a counter that measures a charge time during which the integration capacitor is charged and a discharge time during which the integration capacitor is discharged, the A/D conversion circuit converting into digital quantities the charge time and the discharge time measured by the counter, and outputting the digital quantities, and an information processing unit that calculates a state quantity of the organism based on the digital quantities output from the A/D conversion circuit.

DETAILED DESCRIPTION OF THE INVENTION

First Embodiment

An organism quantity measuring apparatus 1 according a first embodiment of the present invention will be described below with reference to FIGS. 1 and 2.

Figure 1:
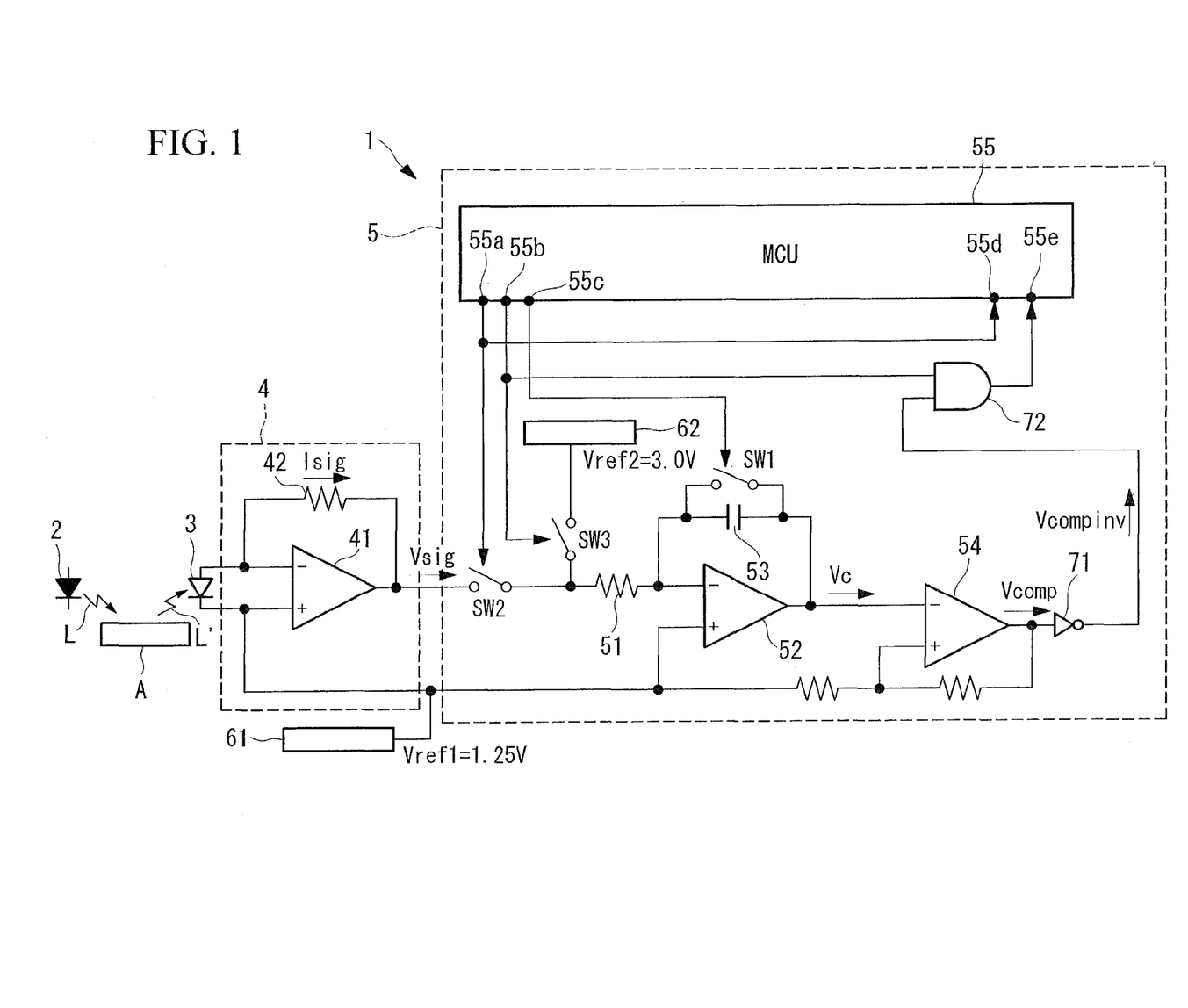
FIG. 1 is a diagram showing the entire configuration of an organism state quantity measuring apparatus according to a first embodiment of the present invention.
Figure 2:
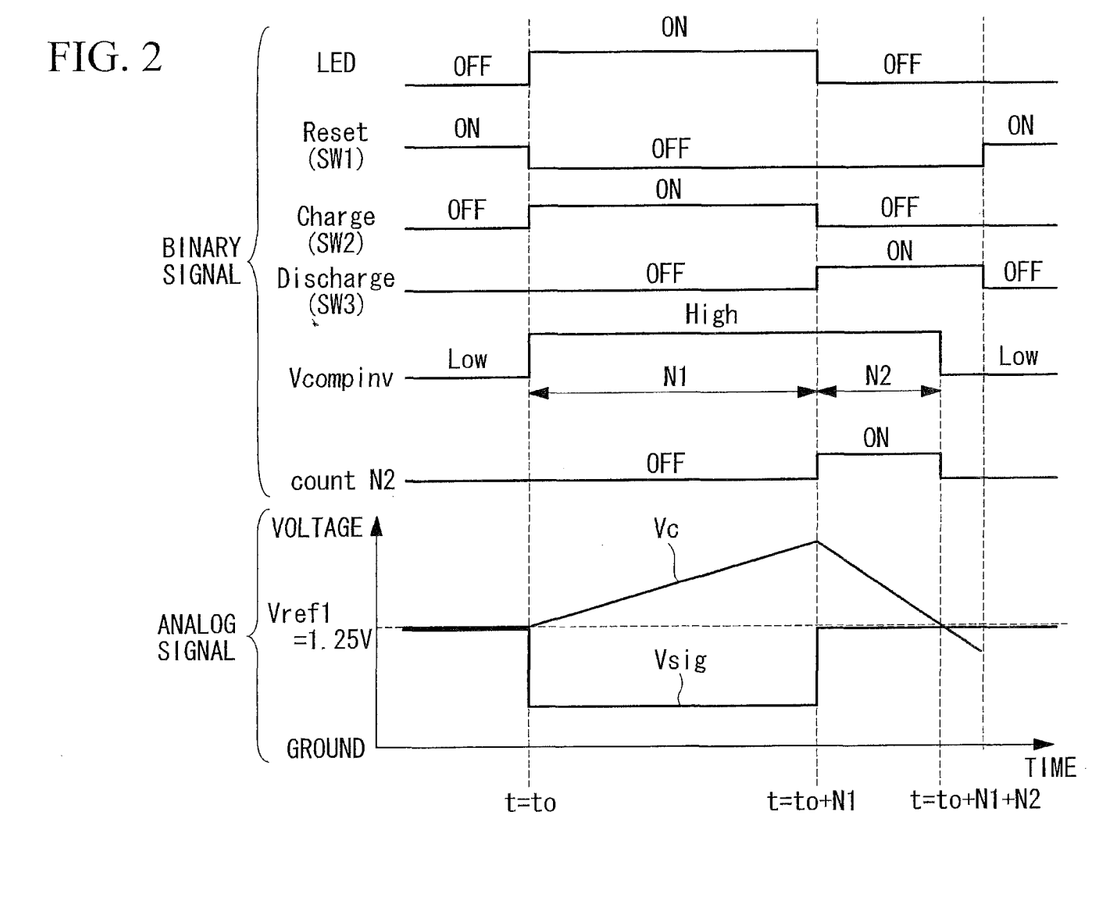
FIG. 2 is a timing charge for explaining the operation of the organism state quantity measuring apparatus shown in FIG. 1.

As shown in FIG. 1, the organism quantity measuring apparatus 1 according the present embodiment has a light emitting diode (an LED, a detecting unit or an illumination light source) 2 that applies illumination light L to an organism or an organism specimen A extracted from an organism (hereinafter referred to as "organism or the like"), a photodiode (a PD or a detecting unit) 3 that detects signal light L' from the organism or the like A, a current-voltage conversion circuit (IV conversion circuit) 4 that converts a signal current Isig from the PD 3 into a signal voltage Vsig, and an A/D conversion circuit 5 of a double integration type that calculates a state quantity of the organism based on the signal voltage Vsig from the IV conversion circuit 4.

The LED 2 applies illumination light L, for example, to blood or a body fluid extracted from a subject as organism or the like A. The LED 2 may alternatively apply illumination light L directly to the organism or the like A existing in a subject.

The PD 3 receives as signal light L' a transmitted part of the illumination light L transmitted through the organism or the like A or a reflected part of the illumination light L reflected by the organism or the like A. The PD 3 outputs the signal current Isig whose magnitude is proportional to the amount of signal light L' received.

The signal light L' detected by the PD 3 includes information indicating a state quantity of the organism, e.g., the value of glucose in blood, the degree of saturation of oxygen in blood or the pulse rate. More specifically, the signal light L' reflected by blood is proportional to the concentration of glucose or the degree of saturation of oxygen in blood and, therefore, the value of glucose or the degree of saturation of oxygen in blood can be measured through the intensity of signal light L'. In another example, the intensity of signal light L' transmitted through a finger end changes in synchronization with the contraction and expansion of blood vessels in the finger end and, therefore, the pulse rate can be measured through change of the signal light L' with time.

The IV conversion circuit 4 has a current-voltage-conversion operational amplifier (hereinafter referred to as "IV operational amplifier") 41 and a conversion resistor 42 connected between an output terminal and an inverting input terminal (hereinafter referred to as "minus input terminal") of the IV operational amplifier 41. The signal current Isig from the PD 3 flows into the conversion resistor 42. The IV operational amplifier 41 is used with a single power supply. A first reference voltage Vref1 generated by a first reference voltage generation circuit 61 is applied to a non-inverting input terminal (hereinafter referred to as "plus input terminal") of the IV operational amplifier 41. In the present embodiment, the first reference voltage Vref1 is assumed to be 1.25 V. When the signal current Isig is input from the PD 3 to the IV conversion circuit 4, the IV conversion circuit 4 outputs the signal voltage Vsig=1.25 V−Isig×Riv. Riv in this expression is the resistance value of the conversion resistor 42.

A/D conversion circuit 5 has an integration resistor 51, an integration operational amplifier 52, an integration capacitor 53, a comparator 54 and a micro control unit (MCU) 55.

The integration resistor 51 is connected to the output terminal of the IV operational amplifier 41 through a switch SW2, and the signal voltage Vsig from the IV conversion circuit 4 is input to the integration resistor 51.

The integration operational amplifier 52 also has the first reference voltage Vref1 applied to its plus input terminal, as does the IV operational amplifier 41.

The integration capacitor 53 is connected between a minus terminal and an output terminal of the integration operational amplifier 52. When a switch SW1 is turned on, a charge voltage Vc on the integration capacitor 53 in an initial state is made equal to the first reference voltage Vref1. When the switch SW2 is turned on to input the signal voltage Vsig from the IV conversion circuit 4 while the switches SW1 and SW3 are in the off state, the integration capacitor 53 is charged by the differential voltage between the signal voltage Vsig and the first reference voltage Vref1, thereby generating the charge voltage Vc.

Next, when the switch SW3 is turned on after charging while the switches SW1 and SW2 are in the off state, the charge on the integration capacitor 53 at the charge voltage Vc is discharged to a second reference voltage circuit 62. In the present embodiment, a second reference voltage Vref2 generated by the second reference voltage circuit 62 is assumed to be 3.0 V. The switch SW1 is thereafter turned on to reset the charge voltage Vc on the integration capacitor 53 to the first reference voltage Vref1.

The comparator 54 also has the first reference voltage Vref1 applied to its plus input terminal, as does the IV operational amplifier 41. An output voltage Vcomp from the comparator 54 is thereby kept low when an integrated voltage Vc higher than the first reference voltage Vref1 is being output from the integration operational amplifier 52, i.e., during charge of the integration capacitor 53 and during a time period from a start of discharge of the integration capacitor 53 to a moment at which the charge voltage Vc reaches the first reference voltage Vref1 by dropping. The output voltage Vcomp is high when the voltage Vc is out of this range.

A NOT circuit 71 is provided in a stage following the comparator 54. When the output voltage Vcomp from the comparator 54 is high, a digital signal at low level is output from the NOT circuit 71. When the output voltage Vcomp from the comparator 54 is low, a digital signal at high level is output from the NOT circuit 71. Vcompinv represents the output from the NOT circuit 71.

The MCU 55 incorporates a central processing unit (CPU), a storage unit, a timer and a counter, not shown in the diagram. The MCU 55 also has an input section and an output section. A program in which a processing procedure is recorded is stored in the storage unit in the MCU. The CPU reads out and executes the program to perform control and processing, for example, for output of a signal from the output section, measurement of time with the counter and calculation of signals input to the input section, as described below.

The output section has a charge output terminal (charge) 55a, a discharge output terminal (discharge) 55b and a reset output terminal (reset) 55c. The input section has a charge time input terminal (count N1) 55d and a discharge time input terminal (count N2) 55e. On command signals for turning on are respectively output from the charge output terminal 55a to the switch SW2, from the discharge output terminal 55b to the switch SW3, and from the reset output terminal 55c to the switch SW1.

From the charge output terminal 55a, a charge time measuring command signal for measuring the time during which the integration capacitor 53 is charged is also output to the charge time input terminal 55d, while the on command signal is simultaneously output. The counter is thereby caused to count the number of clock signal pulses output from a clock with a constant period, thereby measuring a count N1 of the time during which the integration capacitor 53 is charged. A predetermined time period is set in the MCU 55 in advance as the time during which the integration capacitor 53 is charged. However, the count N1 of the time during which the integration capacitor 53 is actually charged may be taken and used in calculation to enable the state quantity to be measured with improved accuracy.

From the discharge output terminal 55b, a discharge time measuring command signal for taking a discharge time count N2 is also output to the discharge time input terminal 55e, while the on command signal is simultaneously output. Through an AND circuit 72 in a stage upstream of the discharge time input terminal 55e, the discharge time measuring command signal output is input to the discharge time input terminal 55e when the output voltage Vcompinv from the NOT circuit 71 is high. Thus, the counter measures the discharge time count N2 from a start of discharge of the integration capacitor 53 to a moment at which the charge voltage Vc reaches the first reference voltage Vref1 by dropping.

The MCU 55 calculates the signal voltage Vsig of the IV conversion circuit 4 by the following expression (1) from the charge time count N1 and the discharge time count N2 measured by the counter.

$$V\text{sig}=(V\text{ref2}-V\text{ref1}) \times N2/N1 \tag{1}$$

Further, the MCU 55 calculates the signal current Isig from the PD 3 by the following expression (2) from the calculated signal voltage Vsig.

$$I\text{sig}=V\text{sig}/Riv \tag{2}$$

The MCU 55 calculates the state quantity of the organism from the signal current Isig obtained by expression (2) based on a function of the value of the signal current Isig from the PD 3 and the state quantity of the organism stored in the storage unit, and makes a display device or the like (not shown) display the calculated state quantity.

Expression (1) is obtained in the way shown below.

When the integration capacitor 53 is charged, the charge voltage Vc, the applied voltage Vsig and the charge time count N1 are in the relationship shown by the following expression (3). In expression (3), Rint is the resistance value of the integration resistor 51, Cint is the electrostatic capacitance value of the integration capacitor 53, and T is the period of the clock.

$$Vc = \left(\frac{1}{RintCint}\right) * \int Vsig \, dt + 1.25 = \left(\frac{1}{RintCint}\right) * N1 * T * Vsig + 1.25 \tag{3}$$

On the other hand, when the integration capacitor 53 is discharged, the charge voltage Vc, the applied voltage Vref2−

Vref1 and the discharge time count N2 are in the relationship shown by the following expression (4).

$$Vc = \left(\frac{1}{RintCint}\right) * \int (Vref2 - Vref1) dt + 1.25 \quad (4)$$
$$= \left(\frac{1}{RintCint}\right) * N2 * T * (Vref2 - Vref1) + 1.25$$

Since the left-hand sides of expressions (3) and (4) are equal to each other, expression (1) is obtained.

The operation and function of the organism state quantity measuring apparatus 1 thus configured will be described below with reference to the timing chart of FIG. 2.

In the organism state quantity measuring apparatus 1 according to the present embodiment, when the LED 2 is not emitting light, i.e., the organism state quantity is not being measured (t<t0), the switch SW1 is on, and thus the charge voltage Vc of the integration capacitor 53 is reset.

When lighting the LED 2 (t=t0), the organism state quantity measuring apparatus 1 according to the present embodiment maintains the switch SW1 in the off state, maintains the switch SW2 in the on state, integrates the signal voltage Vsig from the PD 3 over the charge time count N1 with the integration capacitor 53, and measures the charge time count N1 (t0≤t≤t0+N1). After integrating the signal voltage Vsig (t0=t0+N1), the organism state quantity measuring apparatus 1 discharges the integration capacitor 53 by turning on the switch SW3 and measures the discharge time count value N2 with respect to the integrated signal voltage Vsig (t0+N1≤t≤t0+N1+N2).

The ratio of the charge time count N1 to the discharge time count N2 is in directly proportional to the signal voltage Vsig from the IV conversion circuit 4, i.e., the quantity of signal light L' from the organism or the like A detected with the PD 3. Therefore the organism state quantity measuring apparatus 1 can calculate the state quantity of the organism from the measured charge time count N1 and discharge time count N2 and the known characteristic values of the circuit elements. Also, noise contained in the signal voltage Vsig can be smoothed by integrating the signal voltage Vsig with respect to time, and a measurement error due to noise can be eliminated.

In this case, in the present embodiment, the value of the calculated signal current Isig from the PD 3 is independent of the resistance value Rint of the integration resistor 51 and the electrostatic capacitance value Cint of the integration capacitor 53, as shown by expressions (1) and (2). The reason for this is as follows. In the double-integration-type A/D conversion circuit 5, charge and discharge by the signal voltage Vsig are performed by using the common integration capacitor 53 and integration resistor 51. Therefore, even if the resistance value Rint or the electrostatic static capacitance value Cint is changed, charge and discharge are performed with the same time constant and the ratio of the charge time count N1 and the discharge time count N2 is uniquely determined with respect to the signal voltage Vsig. Thus, advantageously, an accurate measured value of the state quantity can be obtained at all times even if the characteristic values of the integration resistor 51 and the integration capacitor 53 are changed with time by the operating time or the surrounding environment.

Second Embodiment

An organism state quantity measuring apparatus 1 according to a second embodiment of the present invention will be described with reference to FIGS. 3 to 6.

Description will be made mainly of the points of difference of the second embodiment from the above-described first embodiment. The components that the second embodiment and the first embodiment have in common are indicated by the same reference numerals and the description for them will not be repeated.

Figure 3:
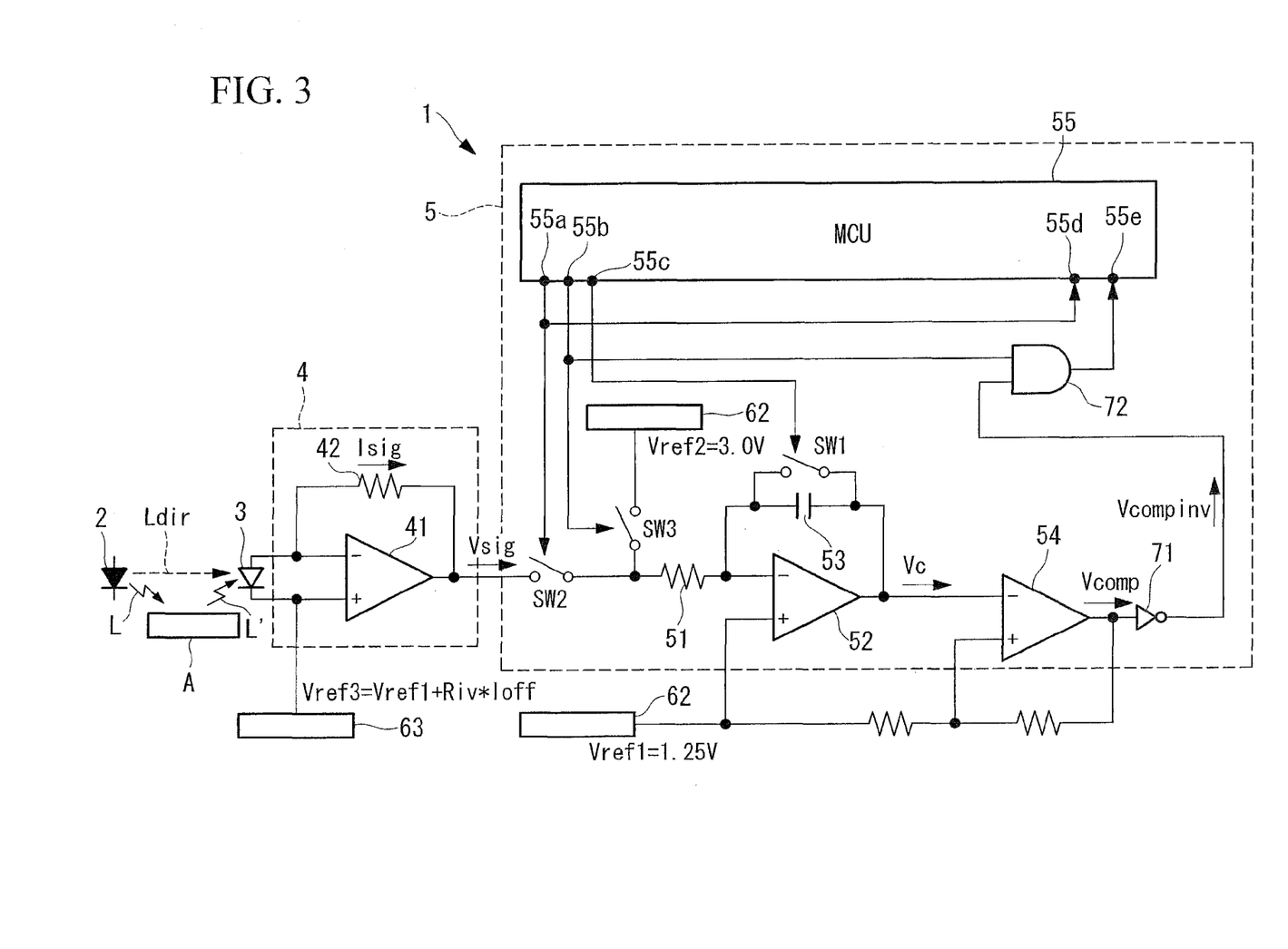
FIG. 3 is a diagram showing the entire configuration of an organism state quantity measuring apparatus according to a second embodiment of the present invention.

The organism state quantity measuring apparatus 1 according to the present embodiment differs from that according to the first embodiment in that, as shown in FIG. 3, different reference voltages Vref1 and Vref3 are respectively applied to the integration operational amplifier 52 and the IV operational amplifier 41.

The integration operational amplifier 52 has the first reference voltage Vref1 applied to its plus input terminal, as does that in the first embodiment.

The IV operational amplifier 41 has the third reference voltage Vref3 applied shown by the following expression (5).

$$Vref3 = Vref1 + Riv \times Ioff \quad (5)$$

Figure 4:
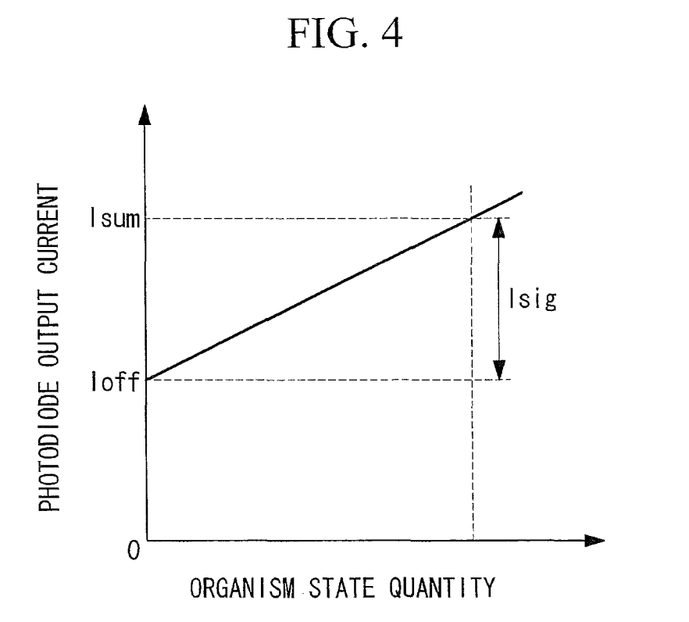
FIG. 4 is a graph showing an offset current in photodiode.

Ioff in this expression is an output current from the PD 3 produced from direct light Ldir that is a part of illumination light L from the LED 2 not applied to the organism or the like A but directly entering the PD 3 (hereinafter referred to as "offset current Ioff"). That is, in a situation where the PD 3 detects direct light Ldir from the LED 2 because of a way in which the PD 3 and the LED 2 are placed, for example, a certain amount of offset current Ioff is output from the PD 3 even under a condition in the absence of the organism or the like A. In this case, the total output current Isum from the PD 3 is the sum of the signal current Isig due to signal light L' from the organism or the like A to be measured and the offset current Ioff, as shown in FIG. 4. As the value of the offset current Ioff, the value of the output current from the PD 3 measured when the LED 2 is lighted under the condition in the absence of the organism or the like A, for example, can be used.

Figure 5:
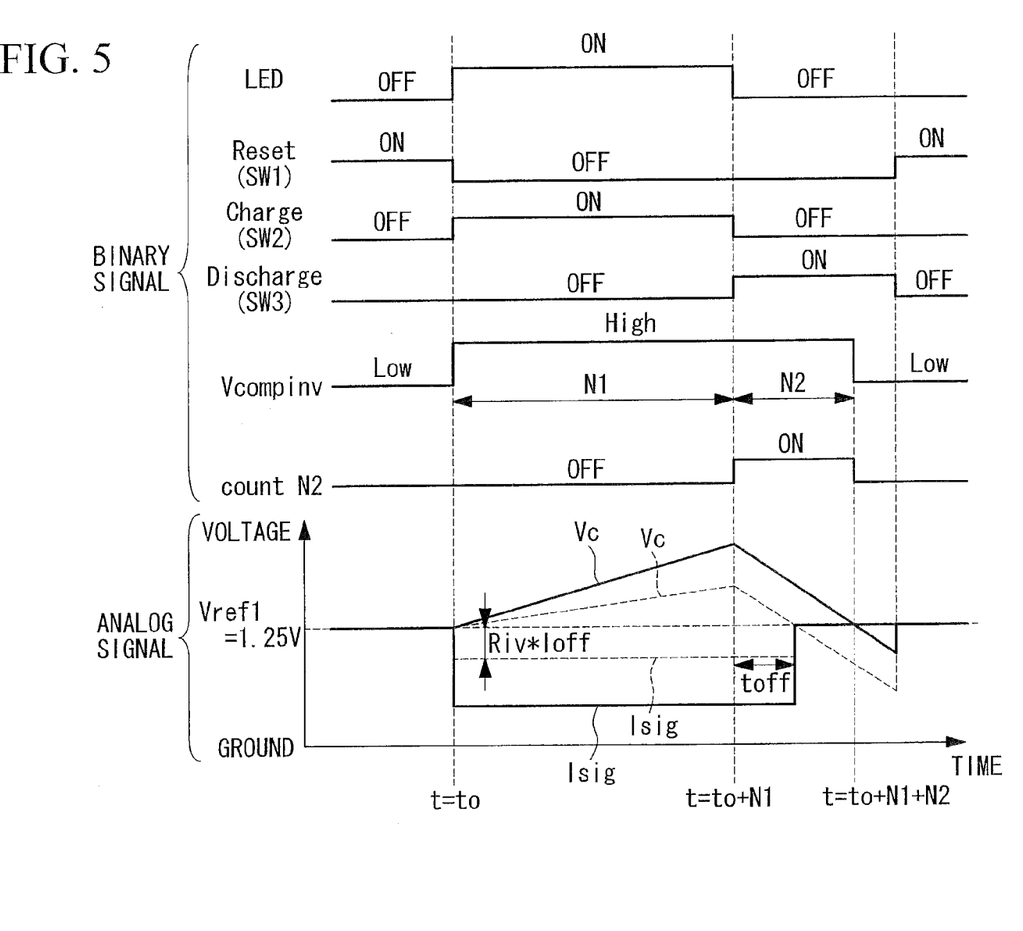
FIG. 5 is a timing charge for explaining the operation of an integration capacitor in a case where an offset current exists in an output current from the photodiode in the arrangement of the organism state quantity measuring apparatus shown in FIG. 1.

In the case where the offset current Ioff exists in the PD 3 in the arrangement of the organism quantity value measuring apparatus 1 according to the first embodiment, if the LED 2 is lighted even though the organism or the like A is not measured, the charge voltage Vc on the integration capacitor 53 is increased by the offset voltage Voff=Riv×Ioff output from the IV conversion circuit 4 as shown by the dotted line in FIG. 5. As a result, when the organism or the like A is measured, the integration capacitor 52 discharge time count N2 is increased by the increase (toff in FIG. 5) in charge voltage Vc due to the offset voltage Voff, as indicated by the solid line in FIG. 5.

Thus, there is a problem that with increase in the time during which the discharge time count N2 is measured, the power consumption is unnecessarily increased. Also, there is a need to select a capacitor and a resistor having large characteristic values Cint and Rint as integration capacitor 52 and integration resistor 51 in consideration of the offset voltage Voff. There is, therefore, another problem that noise is increased, the sizes of the circuit elements 51 and 52 are increased and an increase in overall size of the apparatus 1 results.

Figure 6:
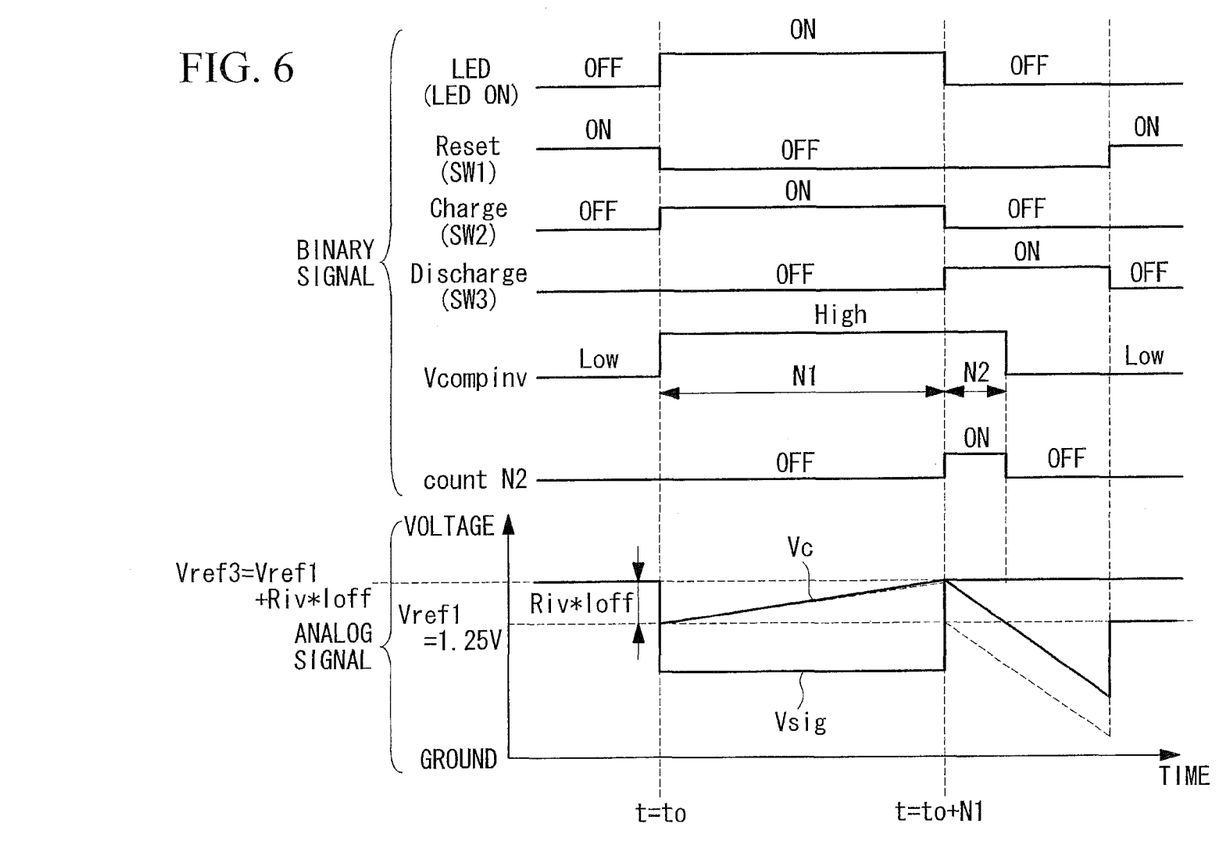
FIG. 6 is a timing chart for explaining the operation of the organism state quantity measuring apparatus shown in FIG. 3.

In contrast, in the arrangement of the organism state quantity measuring apparatus 1 according to the present embodiment, the third reference voltage Vref3 is applied to the IV operational amplifier 41 to output from the IV conversion circuit 4 the voltage from which the offset voltage Voff has been removed, as shown in FIG. 6. The integration capacitor 53 discharge time count N2 is thereby limited to the value corresponding to the signal voltage Vsig necessary for measurement of the state quantity. As a result, advantageously, the increase in power consumption can be avoided.

Other Embodiments

In the above-described first and second embodiments, the connection relationship between the PD 3 and the IV operational amplifier 41 may be reversed so that the signal current Isig is drawn in from the conversion resistor 42. In such a case, the signal voltage Vsig from the IV conversion circuit 4 is positive with respect to the reference voltages Vref1 and Vref3. Also, the reference voltage Vref3 in the second embodiment is as shown by $$Vref3 = Vref1 - Riv*Ioff \quad (5)'$$

While in the first and second embodiments the IV operational amplifier 41 is used with a single power supply and reference voltages Vref1 and Vref3 are applied, the arrangement may alternatively be such that the IV operational amplifier 41 is used with two power supplies and one of the reference voltages Vref1 and Vref3 is set to zero.

Also, in the first and second embodiments, an excitation light source that applies light for excitation of a fluorescent material may be provided in place of the LED 2 and fluorescence from the fluorescent material borne on the organism or the like A in advance may be detected with the PD 3.

An organism molecule in the organism specimen, for example, may be marked in advance with a fluorescent material in this way to enable measurement of the concentration of the organism molecule as an organism state quantity.

Figure 7:
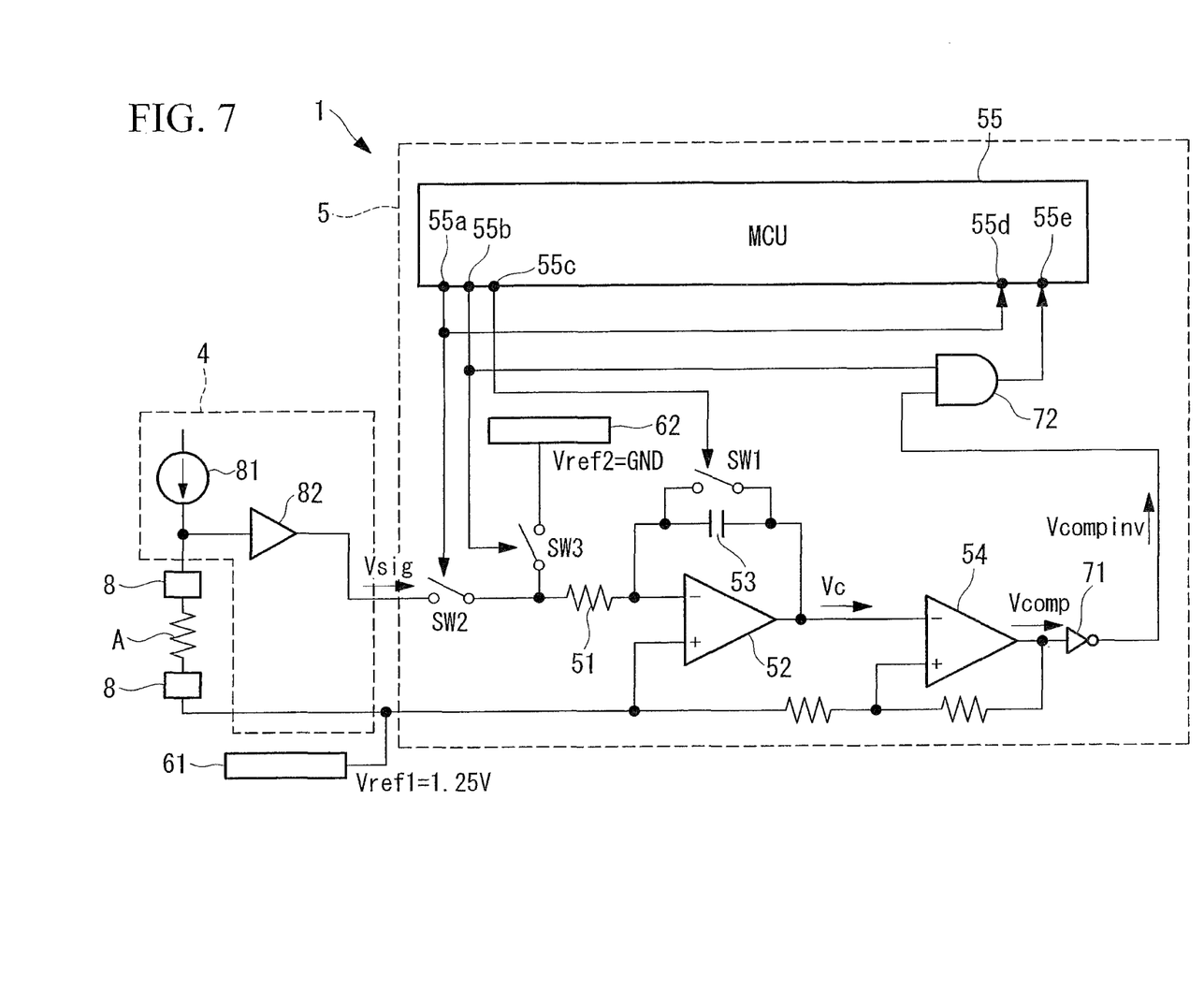
FIG. 7 is a diagram showing an arrangement including a pair of electrode as a modification of the detecting unit.

Also, while the LED 2 and the PD 3 are used as detecting units in the first and second embodiments, two or more electrodes may be used in place of the LED 2 and the PD 3. For example, a pair of positive and negative electrodes 8 are disposed in contact with the organism or the like A and a constant-current circuit 81 causes a constant current to flow between the electrodes 8. The potential between the electrodes 8 generated at this time is received a buffer 82 having a low input impedance. The potential generated between the electrodes 8 is changed by the impedance of the organism or the like A. An output from the buffer 82 is input as output voltage Vsig to the A/D conversion circuit 5.

An impedance can be measured as an organism state quantity this way.

In the first and second embodiments, any of the concentrations of amino acids, the concentrations of stomach/intestine hormones, the concentrations of other hormones, the PH of blood, the concentration of glucose in blood and the concentration of glucose in intertissue fluid can also be measured as the organism state quantity.

The present invention described below is derived from the above-described embodiments.

According to one aspect of the present invention, there is provided an organism state quantity measuring apparatus including a detecting unit that detects information indicating a state of an organism from the organism or an organism specimen extracted from the organism and outputs the detected information as a current, a current-voltage conversion circuit that converts the current output from the detecting unit into a voltage, a double-integration-type A/D conversion circuit having an integration capacitor that is charged based on a voltage output from the current-voltage conversion circuit and is thereafter discharged, and a counter that measures a charge time during which the integration capacitor is charged and a discharge time during which the integration capacitor is discharged, the A/D conversion circuit converting into digital quantities the charge time and the discharge time measured by the counter, and outputting the digital quantities, and an information processing unit that calculates a state quantity of the organism based on the digital quantities output from the A/D conversion circuit.

According to the one aspect of the present invention, the current-voltage conversion circuit (IV conversion circuit) converts the current output by the detecting unit into a voltage, and the integration capacitor is charged based on the voltage output from the current-voltage conversion circuit and is thereafter discharged. Here, the ratio of the integration capacitor discharge time to the integration capacitor charge time depends on the output voltage from the Iv conversion circuit, i.e., the current output from the detecting unit. Therefore the information processing unit can calculates the state quantity of the organism from the digital quantities of the charge time and discharge time measured by the counter.

In this case, since charge and discharge of the integration capacitor are performed through a common path in the double-integration-type A/D conversion circuit, the ratio of the discharge time to the charge time is constant even when the characteristic values of circuit elements in the path are changed, as long as the output voltage from the current-voltage conversion circuit is constant. That is, even if the characteristic values of the circuit elements are changed with time, a measured value of the state quantity can be obtained with stability at all times independently of the changes.

In the organism state quantity measuring apparatus according to another aspect, the current-voltage conversion circuit converts the current output from the detecting unit into a voltage based on a first reference voltage, and the double-integration-type A/D conversion circuit discharges the integration capacitor based on a second reference voltage different from the first reference voltage.

In the organism state quantity measuring apparatus according to still another aspect, the A/D conversion circuit operates based on the first reference voltage, and the current-voltage conversion circuit converts the current output from the detecting unit into a voltage based on a third reference voltage different from the first reference voltage. In a case where the current-voltage conversion circuit outputs a negative voltage with respect to the third reference voltage, the third reference voltage is set higher than the first reference voltage. In a case where the current-voltage conversion circuit outputs a positive voltage with respect to the third reference voltage, the third reference voltage is set lower than the first reference voltage.

With this arrangement, in a case where an offset current other than the current due to the information from the organism is included in the current output from the detecting unit, the increase in the absolute value of the voltage output from the IV conversion circuit due to the offset current can be suppressed. As a result, the integration capacitor discharge time is reduced and the time during which the discharge time is measured by the counter is thereby reduced, thus suppressing the increase in power consumption.

In the organism state quantity measuring apparatus according to a further aspect of the present invention, the detecting unit includes an illumination light source that applies illumination light to the organism or the organism specimen, and a photodiode that receives a reflected part of the illumination light reflected by the organism or the organism specimen or a transmitted part of the illumination light transmitted through the organism or the organism specimen, and outputs the reflected or transmitted light as a current.

With this arrangement, a state quantity such as the concentration of an organism molecule contained in the organism or the organism specimen can be measured based on the intensity of the reflected light or the transmitted light.

In the organism state quantity measuring apparatus according to still a further aspect of the present invention, the detecting unit includes at least two electrodes that are brought into contact with the organism or the organism specimen to detect a current flowing through the organism or the organism specimen.

With this arrangement, a state quantity such as the pulse rate can be measured based on the magnitude of the current flowing through the organism or the organism specimen or changes in the magnitude of the current.

In the organism state quantity measuring apparatus according to still a further aspect of the present invention, the detecting unit includes an excitation light source that irradiates the organism or the organism specimen with excitation light for excitation of a fluorescent material borne on the organism or the organism specimen, and a photodiode that receives fluorescence from the fluorescent material and outputs a current corresponding to the fluorescence.

With this arrangement, a state quantity such as the concentration of an organism molecule contained in the organism or the organism specimen can be measured based on the intensity of fluorescence.

What is claimed is:

1. An organism state quantity measuring apparatus comprising:
    a detector comprising hardware that detects information indicating a state of an organism from the organism or an organism specimen extracted from the organism and outputs the detected information as a current;
    a current-voltage conversion circuit that converts the current output from the detector into a voltage;
    a double-integration-type A/D conversion circuit having an integration capacitor that is charged based on a voltage output from the current-voltage conversion circuit and is thereafter discharged, and a counter that measures a charge time during which the integration capacitor is charged and a discharge time during which the integration capacitor is discharged, the A/D conversion circuit converting into digital quantities the charge time and the discharge time measured by the counter, and outputting the digital quantities; and
    an information processor comprising hardware that calculates a state quantity of the organism based on a ratio of the digital quantities of the charge time output from the A/D conversion circuit to the digital quantities of the discharge time output from the A/D conversion circuit.

2. The organism state quantity measuring apparatus according to claim 1, wherein
    the current-voltage conversion circuit converts the current output from the detector into a voltage based on a first reference voltage, and
    the double-integration-type A/D conversion circuit discharges the integration capacitor based on a second reference voltage different from the first reference voltage.

3. The organism state quantity measuring apparatus according to claim 1, wherein the detector includes:
    an illumination light source that applies illumination light to the organism or the organism specimen; and
    a photodiode that receives a reflected part of the illumination light reflected by the organism or the organism specimen or a transmitted part of the illumination light transmitted through the organism or the organism specimen, and outputs the reflected or transmitted light as a current.

4. The organism state quantity measuring apparatus according to claim 1, wherein the detector includes at least two electrodes that are brought into contact with the organism or the organism specimen to detect a current flowing through the organism or the organism specimen.

5. The organism state quantity measuring apparatus according to claim 1, wherein the detector includes:
    an excitation light source that irradiates the organism or the organism specimen with excitation light for exciting a fluorescent material borne on the organism or the organism specimen; and
    a photodiode that receives fluorescence from the fluorescent material and outputs a current corresponding to the fluorescence.

6. An organism state quantity measuring apparatus, comprising:
    a detector comprising hardware that detects information indicating a state of an organism from the organism or an organism specimen extracted from the organism and outputs the detected information as a current;
    a current-voltage conversion circuit that converts the current output from the detector into a voltage;
    a double-integration-type A/D conversion circuit having an integration capacitor that is charged based on a voltage output from the current-voltage conversion circuit and is thereafter discharged, and a counter that measures a charge time during which the integration capacitor is charged and a discharge time during which the integration capacitor is discharged, the A/D conversion circuit converting into digital quantities the charge time and the discharge time measured by the counter, and outputting the digital quantities; and
    an information processor comprising hardware that calculates a state quantity of the organism based on the digital quantities output from the A/D conversion circuit;
    wherein:
    the double-integration-type A/D conversion circuit operates based on a first reference voltage;
    the current-voltage conversion circuit converts the current output from the detecting unit detector into a voltage based on a third reference voltage different from the first reference voltage;
    in a case where the current-voltage conversion circuit outputs a negative voltage with respect to the third reference voltage, the third reference voltage is set higher than the first reference voltage; and
    in a case where the current-voltage conversion circuit outputs a positive voltage with respect to the third reference voltage, the third reference voltage is set lower than the first reference voltage.

* * * * *